United States Patent [19]

Walker et al.

[11] Patent Number: 4,741,853

[45] Date of Patent: May 3, 1988

[54] SOLID BLEACHING BLOCK

[75] Inventors: Adrian W. Walker; David E. Clarke, both of Wirral, Great Britain

[73] Assignee: Lever Brothers Company, New York, N.Y.

[21] Appl. No.: 13,514

[22] Filed: Feb. 11, 1987

[30] Foreign Application Priority Data

Feb. 12, 1986 [GB] United Kingdom ............... 8603440

[51] Int. Cl.$^4$ ............................................. C11D 7/54
[52] U.S. Cl. ....................................... 252/96; 252/94; 252/134; 252/174; 252/186.1; 252/186.43; 4/227; 422/37
[58] Field of Search ............... 252/94, 96, 134, 174, 252/186.1, 186.43, DIG. 16; 4/227, 228; 422/37

[56] References Cited

U.S. PATENT DOCUMENTS

| 3,607,761 | 9/1971 | Feighner et al. | 252/134 |
| 4,490,269 | 12/1984 | Gallopo | 252/94 |
| 4,668,475 | 5/1987 | Meloy | 252/94 |

FOREIGN PATENT DOCUMENTS

| 4991 | 10/1979 | European Pat. Off. . |
| 140692 | 5/1985 | European Pat. Off. . |
| 157464 | 10/1985 | European Pat. Off. . |

*Primary Examiner*—Paul Lieberman
*Assistant Examiner*—Hoa Van Le
*Attorney, Agent, or Firm*—Milton L. Honig; James J. Farrell

[57] ABSTRACT

The present invention provides a solid bleaching block on the basis of an alkali metal monopersulphate for use in an in-cistern dispensing device, also comprising at least 5% by weight of an alkaline earth metal soap. By the use of these soaps, blocks are obtained which release the bleaching agent at an acceptable rate yet maintain their block structure.

3 Claims, No Drawings

SOLID BLEACHING BLOCK

The present invention relates to a solid bleaching block for use in a device which is used in cisterns for the automatic dosing of controlled amounts of bleaching materials into the WC-cisterns when these are flushed. Such a device is partially immersed in the flush water in the cistern, and contains a compartment which can contain a solid bleaching block. A typical example of such an in-cistern device is described in our published European Patent Application No. 0 140 692, which is hereby incorporated by way of reference.

By permitting ingress of flush water through an aperture in the compartment, the bleaching materials can dissolve in the flush water, and by permitting egress of the thus obtained solution through another aperture, controlled amounts of active bleaching agents are released to the water which when flushed from the cistern into the lavatory bowl can exert their cleaning and bleaching action on the surface of the bowl and in the bottom of the bowl.

Most of the solid bleaching blocks known and used for this purpose contain a chlorine-type bleaching agent, but it has also already been proposed to use an oxygen-type bleaching agent for this purpose. Thus, it has been proposed in European Patent Application No. 0 004 991 to use sodium perborate or potassium monopersulphate as bleaching agent in such a solid bleaching block, together with a suitable inorganic stabilizing salt. Recently, it has been proposed in European Patent Application No. 0 157 464 to prepare a denture-cleansing tablet comprising an anhydrous perborate, a perborate monohydrate and a monopersulphate. Lubricants are also included to release the tablet from the tableting die, such as alkali metal soaps and alkaline earth metal soaps, in small amounts. The use of monopersulphate in denture-cleaning blocks usually involves the use of magnesium carbonate or similar material both as a flow aid in the monopersulphate and to promote block disintegration. Such material is, however, unsuitable for use in solid bleaching blocks for in-cistern devices.

The present invention is directed to solid bleaching blocks for use in cisterns wherein the blocks comprise as oxygen-type bleaching agent an alkali metal monopersulphate. It has been found that the inclusion of at least 5% by weight of an alkaline earth metal salt of a $C_{12}$–$C_{24}$ fatty acid in such a block provides for a block which releases its bleaching ingredient at an acceptable rate when in use but which maintains its block structure. In contrast thereto, the use of inorganic salts such as magnesium carbonate, which are primarily used as flow aids for the monopersulphate and, in the case of magnesium carbonate, to get block disintegration, causes rapid block disintegration, and the use of magnesium oxide causes undesirable block swelling. The use of the levels of soaps as described in EP No. 0 157 464 for mould release/lubrication during block making causes too rapid monopersulphate dissolution, even without the block swelling and disintegration problems resulting from interactions with the usual flow aids.

The present invention therefore provides a solid bleach block for use in a device for the automatic dosing of controlled amounts of bleaching agent in WC-cisterns, said block comprising as oxygen-type bleaching agent an alkali metal monopersulphate, the block being characterised in that it contains at least 5% by weight of an alkaline earth metal salt of a $C_{12}$–$C_{24}$ fatty acid.

The amount of the alkaline earth metal salt of the fatty acid present in the block can be as high as 30% by weight, and usually the amount ranges from 5–20, preferably from 5–10% by weight. The alkali metal monopersulphate is preferably potassium monopersulphate, and is desirably used in the form of a triple salt with potassium bisulphate and potassium sulphate. Such salts are commercially available, e.g. under the trade name "Oxone" ex E. I. du Pont de Nemours, or "Caroat" ex Degussa. They should, however, be free from the usual flow aids such as the inorganic salts discussed above. The block generally contains the alkali metal monopersulphate in an amount of 60–95% by weight. Other oxygen-type bleaching agents can also be included if desired. The block further may optionally contain a lubricant or binding agent such as a fatty acid, a nonionic or anionic detergent, a perfume, a colouring agent, inert filling materials and so on. If the nonionic detergent, perfume or colouring material is not stable in the presence of the bleaching agent, they can be included in a separate block in the other half of a two-compartment device. The amounts of these optional ingredients are usually low, and form the balance of the composition of the block if the block does not solely consist of the monopersulphate and alkaline earth metal fatty salt.

A typical example of a block according to the invention is a block, prepared by compressing 93% of particulate potassium monopersulphate with 7% of calcium stearate or magnesium stearate.

The blocks according to the present invention are particularly suitable for use in an in-cistern device as described in our European Patent Application No. 140 692.

We claim:

1. A solid bleaching block for use in an in-cistern device for the automatic dosing of controlled amounts of bleaching materials into the cistern when this is flushed, said block comprising from 60–95% by weight of an alkali metal monopersulphate and from 5–30% by weight of an alkaline earth metal salt of a $C_{12}$–$C_{24}$ fatty acid.

2. The block of claim 1, wherein said alkaline earth metal salt of a $C_{12}$–$C_{24}$ fatty acid is selected from the group consisting of calcium stearate and magnesium stearate.

3. The block of claim 2, comprising 93% by weight of potassium monopersulphate and 7% by weight of calcium stearate or magnesium stearate.

* * * * *